(12) United States Patent
Quill et al.

(10) Patent No.: US 9,662,202 B2
(45) Date of Patent: May 30, 2017

(54) HEART VALVE PROSTHESIS

(71) Applicant: Medtronic, Inc, Minneapolis, MN (US)

(72) Inventors: Jason Quill, Forest Lake, MN (US); Igor Kovalsky, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 137 days.

(21) Appl. No.: 14/519,793

(22) Filed: Oct. 21, 2014

(65) Prior Publication Data

US 2015/0119982 A1    Apr. 30, 2015

Related U.S. Application Data

(60) Provisional application No. 61/895,106, filed on Oct. 24, 2013.

(51) Int. Cl.
*A61F 2/24* (2006.01)

(52) U.S. Cl.
CPC .......... *A61F 2/2409* (2013.01); *A61F 2/2418* (2013.01); *A61F 2230/005* (2013.01); *A61F 2230/008* (2013.01)

(58) Field of Classification Search
CPC ............................. A61F 2/2418; A61F 2/2475
See application file for complete search history.

(56) References Cited

U.S. PATENT DOCUMENTS

| | | | |
|---|---|---|---|
| 5,545,215 A | 8/1996 | Duran | |
| 5,957,949 A | 9/1999 | Leonhardt et al. | |
| 7,101,396 B2 | 9/2006 | Artof et al. | |
| 7,399,315 B2 | 7/2008 | Iobbi | |
| 7,748,389 B2 | 7/2010 | Salahieh et al. | |
| 7,780,725 B2 | 8/2010 | Haug et al. | |
| 7,837,727 B2 | 11/2010 | Goetz et al. | |
| 7,947,075 B2 | 5/2011 | Goetz et al. | |
| 8,449,599 B2 | 5/2013 | Chau et al. | |

(Continued)

FOREIGN PATENT DOCUMENTS

| CA | 2827556 | 7/2012 |
|---|---|---|
| DE | 102006052564 | 12/2007 |

(Continued)

OTHER PUBLICATIONS

Boudjemline et al. "Steps Toward Percutaneous Aortic Valve Replacement" Circulation 2002; 105; 775-558.

(Continued)

*Primary Examiner* — Christian Sevilla
*Assistant Examiner* — Megan Wolf

(57) ABSTRACT

Mitral valve prosthesis are disclosed that include a frame or support structure having an inflow portion, a valve-retaining tubular portion and a pair of support arms. The inflow portion radially extends from a first end of the valve-retaining tubular portion and the pair of support arms are circumferentially spaced apart and radially extend from an opposing second end of the valve-retaining tubular portion. The inflow portion is formed from a plurality of struts that outwardly extend from the first end of the valve-retaining tubular portion with adjacent struts of the plurality of struts being joined, wherein each strut of the plurality of struts has a substantially s-shaped profile and at least one twisted area.

15 Claims, 11 Drawing Sheets

(56) References Cited

U.S. PATENT DOCUMENTS

| | | | |
|---|---|---|---|
| 9,398,951 B2* | 7/2016 | Alkhatib | A61F 2/2418 |
| 2003/0036791 A1 | 2/2003 | Philipp et al. | |
| 2003/0199963 A1 | 10/2003 | Tower et al. | |
| 2003/0199971 A1 | 10/2003 | Tower et al. | |
| 2004/0111111 A1 | 6/2004 | Lin | |
| 2008/0071361 A1 | 3/2008 | Tuval et al. | |
| 2009/0216313 A1 | 8/2009 | Straubinger et al. | |
| 2009/0240320 A1 | 9/2009 | Tuval et al. | |
| 2009/0276027 A1 | 11/2009 | Glynn | |
| 2010/0036479 A1 | 2/2010 | Hill et al. | |
| 2010/0191320 A1 | 7/2010 | Straubinger et al. | |
| 2010/0262231 A1 | 10/2010 | Tuval et al. | |
| 2011/0137397 A1 | 6/2011 | Chau et al. | |
| 2011/0208298 A1 | 8/2011 | Tuval et al. | |
| 2011/0224785 A1* | 9/2011 | Hacohen | A61F 2/2418 623/2.18 |
| 2012/0041550 A1 | 2/2012 | Salahieh et al. | |
| 2012/0078360 A1 | 3/2012 | Rafiee | |
| 2012/0101572 A1 | 4/2012 | Kovalsky et al. | |
| 2012/0303116 A1* | 11/2012 | Gorman, III | A61F 2/2418 623/2.11 |
| 2014/0067054 A1 | 3/2014 | Chau et al. | |
| 2014/0194982 A1 | 7/2014 | Kovalsky et al. | |
| 2014/0222136 A1* | 8/2014 | Geist | A61F 2/2466 623/2.11 |
| 2014/0277563 A1* | 9/2014 | White | A61F 2/82 623/23.7 |
| 2015/0173897 A1* | 6/2015 | Raanani | A61F 2/2418 623/2.11 |

FOREIGN PATENT DOCUMENTS

| | | |
|---|---|---|
| WO | WO2004/019825 | 3/2004 |
| WO | WO2011/057087 | 5/2011 |
| WO | WO2012/061809 | 5/2012 |
| WO | WO2012/095159 | 7/2012 |
| WO | WO 2013/021374 | 2/2013 |
| WO | WO2013/072496 | 5/2013 |
| WO | WO2014/028112 | 2/2014 |

OTHER PUBLICATIONS

Lauten et al., "Experimental Evaluation of the JenaClip Transcatheter Aortic Valve" Catheterization and Cardiovascular Interventions 74:514-519 (2009).

Chau, Mark, U.S. Appl. No. 61/287,099, "Prosthetic Mitral Valve With Subvalvular Anchoring" filed Dec. 16, 2009.

Chau et al. U.S. Appl. No. 61/266,774, "Prosthetic Mitral Valve with Subvalvular Anchoring" filed Dec. 4, 2009.

International Search Report and Written Opinion, Int'l Appl. No. PCT/US2013/045789, Dated Dec. 6, 2013.

PCT/US2014/020876, PCT International Search Report and Written Opinion, mailed Jul. 2, 2014.

* cited by examiner

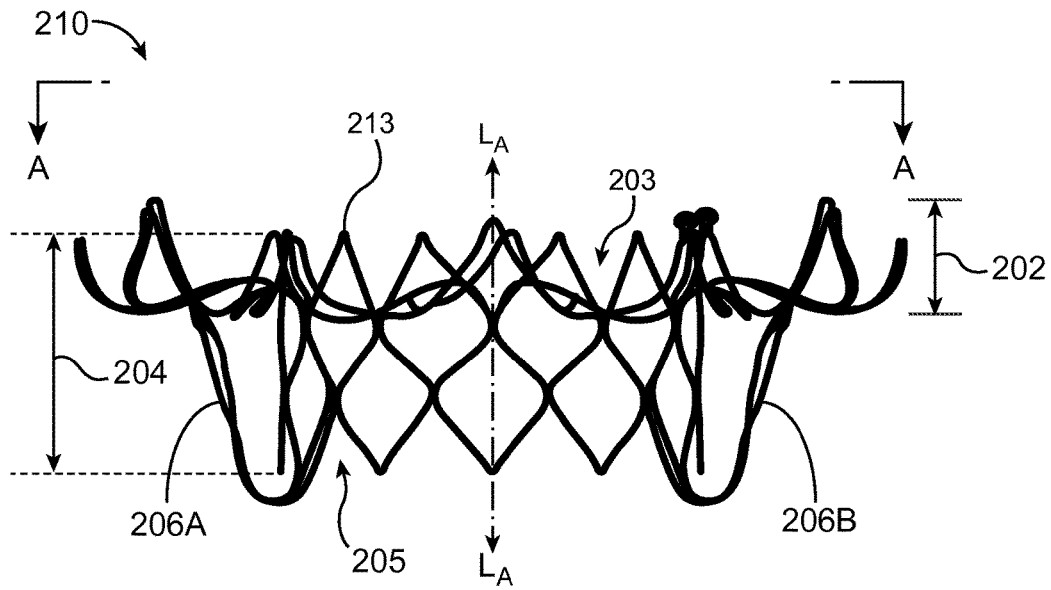
FIG. 3
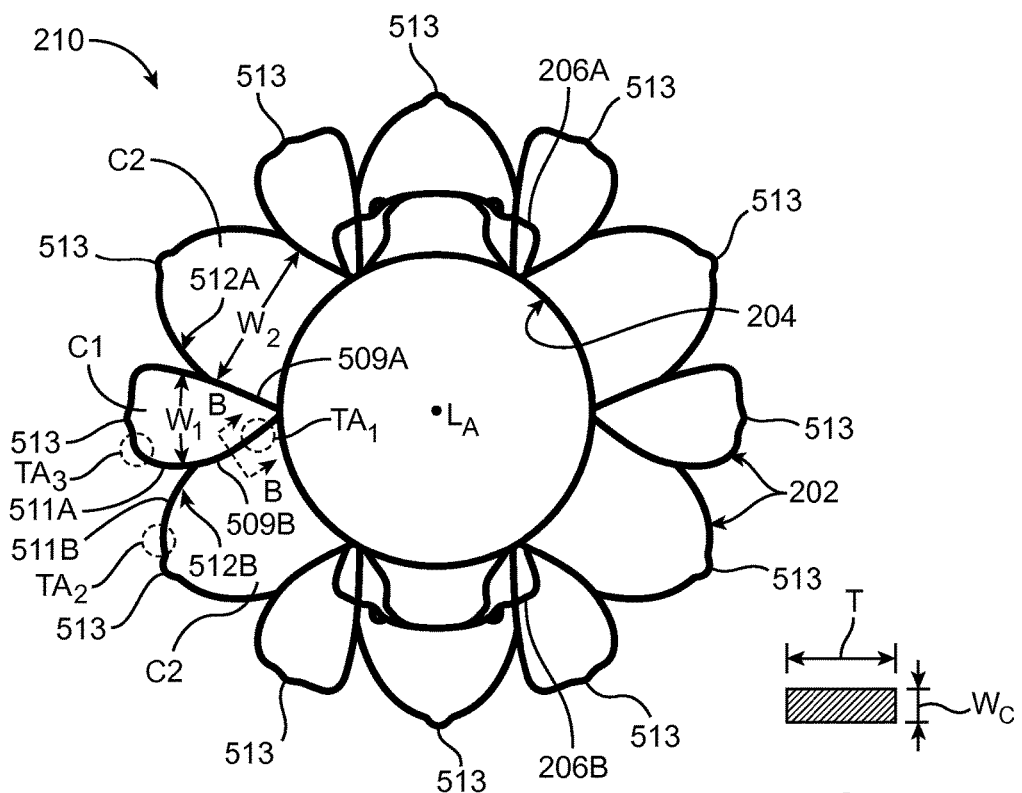
FIG. 3A
FIG. 3B

HEART VALVE PROSTHESIS

CROSS REFERENCE TO RELATED APPLICATIONS

This application claims the benefit of U.S. Appl. No. 61/895,106, filed Oct. 24, 2013, which is incorporated by reference herein in its entirety.

FIELD OF THE INVENTION

The present invention is directed to heart valve prosthesis, and more particularly to a mitral valve prosthesis for use in a transcatheter mitral valve replacement procedure.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al., which is incorporated by reference herein in its entirety.

Although transcatheter delivery methods may provide safer and less invasive methods for replacing a defective native heart valve, preventing leakage between the implanted prosthetic valve and the surrounding native tissue remains a challenge. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site and expanded to its operational state within the diseased heart valve, which may not allow complete conformance of the stent frame within the native heart valve and can be a source of paravalvular leakage (PVL). As well PVL may occur after a heart valve prosthesis is implanted due to movement and/or migration of the prosthesis that can occur during the cardiac cycle. Movement due to changes in chordal tensioning during the cardiac cycle may be particularly problematic for mitral valve prosthesis, as chordal tensioning can axially unseat, lift or rock the prosthesis within or into the atrium resulting in PVL. Accordingly, there is a continued need to provide mitral valve prosthesis having structure that maintains sealing within the native anatomy during the cardiac cycle.

BRIEF SUMMARY OF THE INVENTION

Mitral valve prosthesis according to embodiments hereof includes a frame having a flexible, anatomically conforming inflow portion that is designed to maintain sealing with the atrial surface surrounding the native mitral valve during the cardiac cycle. The frame or support structure defines an inflow portion, a valve-retaining tubular portion and a pair of support arms. The inflow portion radially extends from a first end of the valve-retaining tubular portion and the pair of support arms are circumferentially spaced apart and radially extend from an opposing second end of the valve-retaining tubular portion. The inflow portion is formed from a plurality of struts that outwardly extend from the first end of the valve-retaining tubular portion with adjacent struts of the plurality of struts being, wherein each strut of the plurality of struts has a substantially s-shaped profile and at least one twisted area.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a side view of a frame of the mitral valve prosthesis of FIG. 2.

FIG. 3A is a top or inflow view of the frame of FIG. 3 taken in the direction of line A-A therein.

FIG. 3B is a cross-sectional view of a strut of the frame of FIG. 3A taken along line B-B therein.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, as used herein, the terms "outward" or "outwardly" refer to a position radially away from a longitudinal axis of a frame of the prosthesis and the terms "inward" or "inwardly" refer to a position radially toward a longitudinal axis of the frame of the prosthesis. As well the terms "backward" or "backwardly" refer to the relative transition from a downstream position to an upstream position.

The following detailed description is merely exemplary in nature and is not intended to limit the invention or the application and uses of the invention. Although the description of embodiments hereof are in the context of treatment of heart valves and particularly a mitral valve, the invention may also be adapted for use in other valve replacement procedures where it is deemed useful. Furthermore, there is no intention to be bound by any expressed or implied theory presented in the preceding technical field, background, brief summary or the following detailed description.

Figure 1:
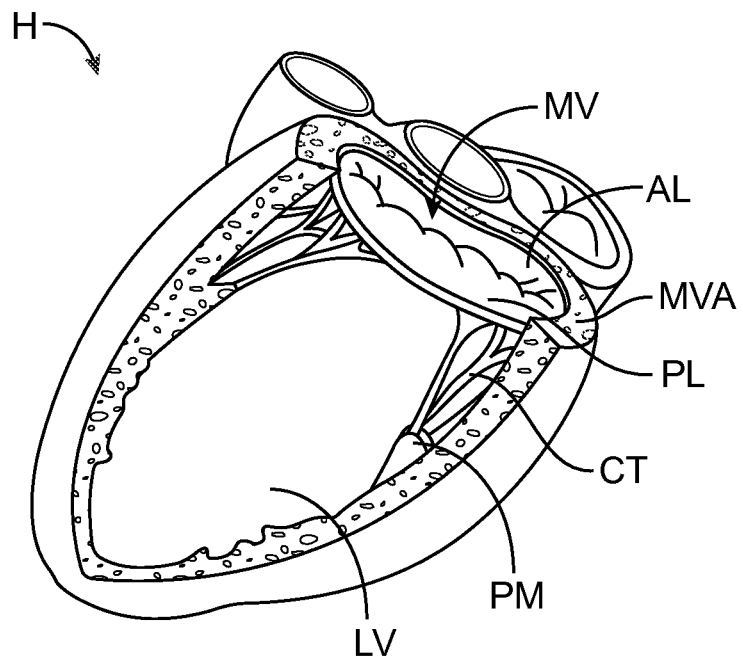
FIG. 1 is a perspective sectional view of a heart that depicts a mitral valve and various structural features related thereto.
Figure 1A:
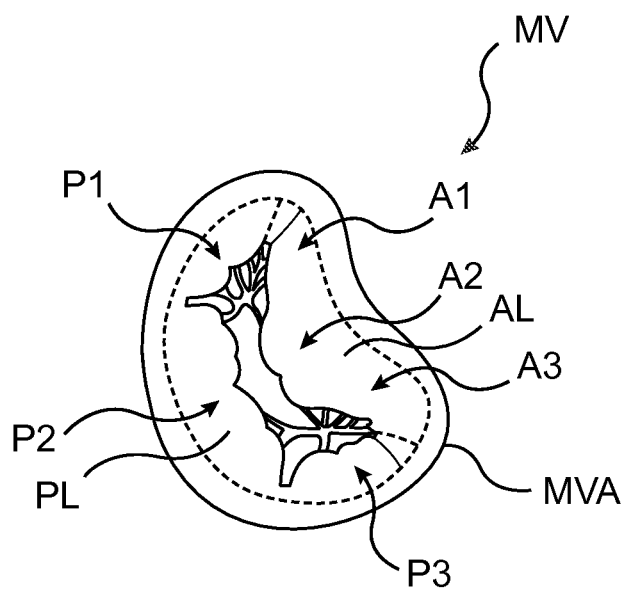
FIG. 1A is a superior view of the mitral valve shown in FIG. 1 isolated from the surrounding heart structure.

FIG. 1 is a perspective sectional view of a heart (H) that depicts a mitral valve (MV) and various structural features related thereto, with FIG. 1A being a superior view of the mitral valve isolated from surrounding heart structure. The mitral valve is found between the left atrium (not shown) and the left ventricle (LV) and is surrounded by and attached to a fibrous atrioventricular ring of the heart that may be more commonly referred to as the mitral valve annulus (MVA). As best shown in FIG. 1A, the mitral valve annulus may be considered to have a D-shape rather than being circular or elliptical. The mitral valve includes anterior and posterior leaflets (AL, PL) that open during diastole to allow blood flow from the left atrium to the left ventricle. During ventricular systole, the anterior and posterior leaflets close to prevent backflow to the left atrium while the mitral valve annulus contracts and reduces its surface area to help provide complete closure of the leaflets. The anterior and posterior leaflets are attached to papillary muscles (PM) within the left ventricle by way of the chordae tendinae (CT), which are strong, fibrous strings or structures attached to the leaflets of the heart on the ventricular side. When the anterior and posterior leaflets of the mitral valve close, the chordae tendinae are tensioned to prevent the leaflets from swinging back into the atrium cavity.

Due to the unique shape of a native mitral valve and the functionality of the structure associated therewith that can cause axial movement of a prosthetic mitral valve during the cardiac cycle, i.e., axial movement that may be caused by the cyclic tensioning of the chordae tendinae and/or contraction of the D-shaped mitral valve annulus during ventricular systole, a mitral valve prosthesis according to embodiments hereof includes a frame having a flexible, anatomically conforming inflow portion that is designed to maintain sealing with the atrial surface surrounding the mitral valve during the cardiac cycle.

Figure 2:
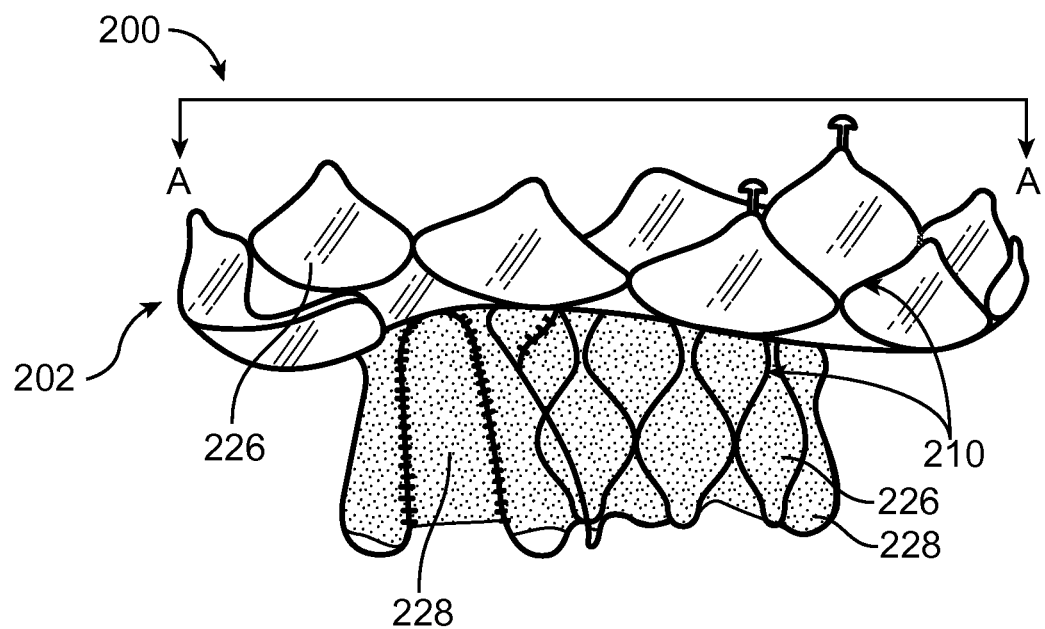
FIG. 2 is a side view of a mitral valve prosthesis in accordance with an embodiment hereof shown in a deployed configuration.
Figure 2A:
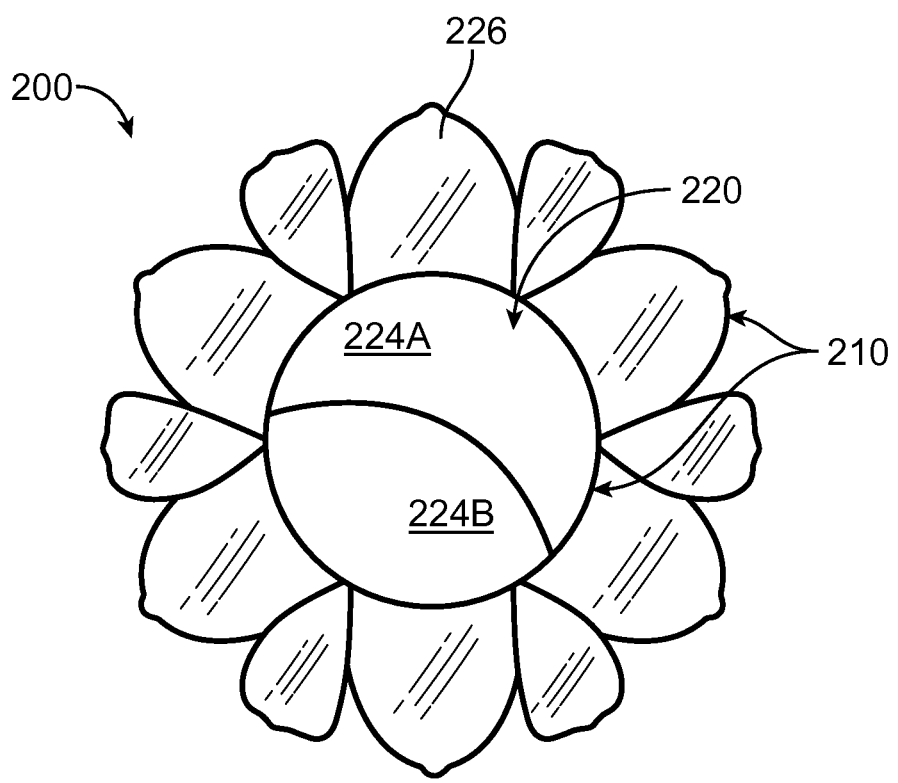
FIG. 2A is a top view of an inflow area of the mitral valve prosthesis of FIG. 2 taken in the direction of line A-A therein.

FIG. 2 is a side view of a mitral valve prosthesis 200 in accordance with an embodiment hereof shown in a deployed configuration, with FIG. 2A being a top view of an inflow area of prosthesis 200 taken in the direction of line A-A in FIG. 2. Prosthesis 200 includes a valve component 220 attached within an interior of a frame or support structure 210. Valve component 220 is a one-way bicuspid replacement valve having first and second valve leaflets 224A, 224B. In another embodiment, valve component 220 may be a one-way tricuspid replacement valve having three valve leaflets. Valve leaflets 224A, 224B are sutured or otherwise securely and sealingly attached to an interior surface of frame 210 and/or to graft material 226, which encloses or lines various portions of frame 210. In embodiments in accordance herewith, graft material 226 secured to frame 210 within an inflow area of prosthesis 200 aids in sealing and graft material 226 secured to frame 210 proximate an outflow area of prosthesis 200 provides a tent-like or hammock structure 228, which functions to reduce or eliminate interaction between frame 210 and the chordae tendinae when prosthesis 200 is implanted within a native mitral valve.

Figure 4:
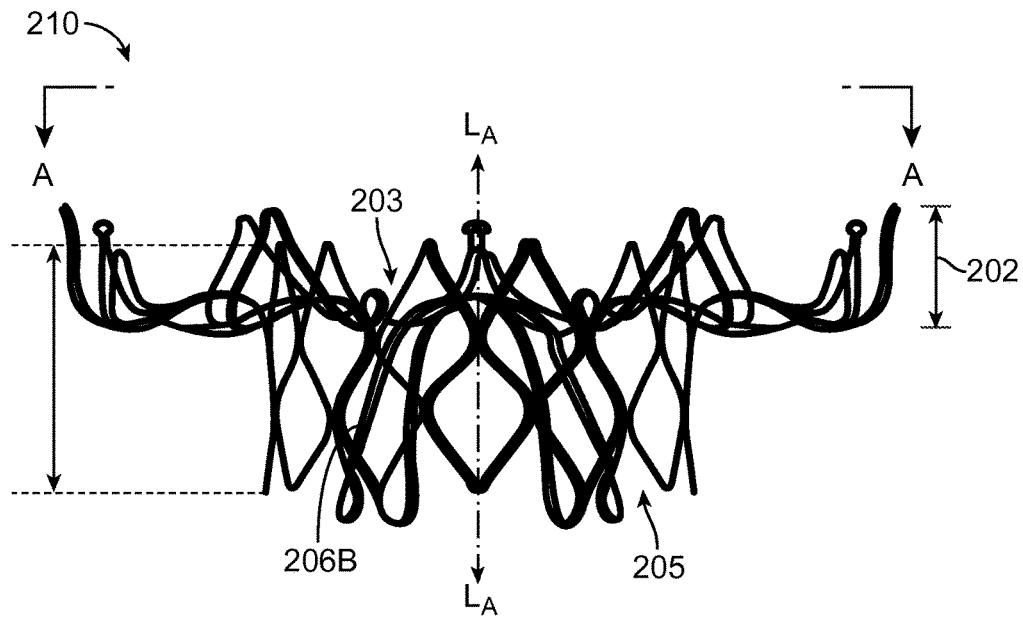
FIG. 4 is a side view of the frame of FIG. 3 rotated 90° about a longitudinal axis $L_A$ thereof from the orientation shown in FIG. 3.
Figure 4A:
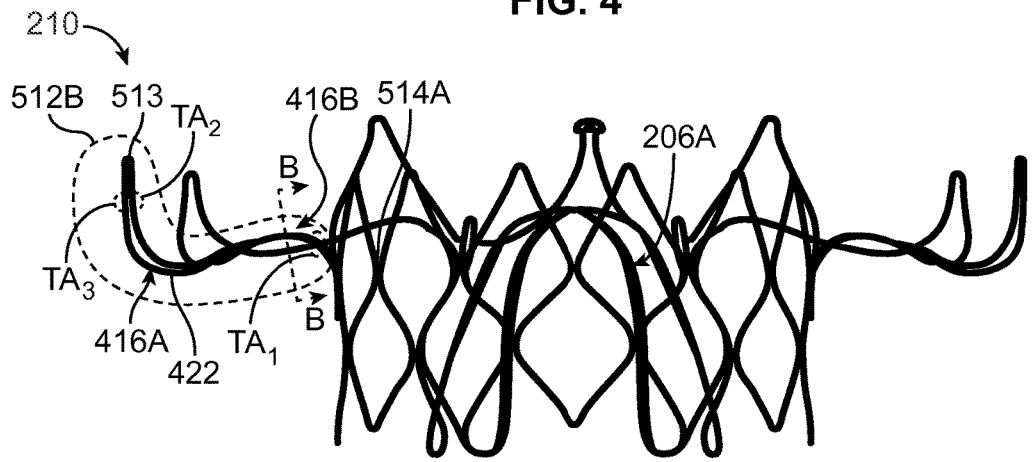
FIG. 4A is a side sectional view of the frame of FIG. 4 taken along line A-A therein that highlights the s-shape feature of the inflow section of the frame.
Figure 4B:
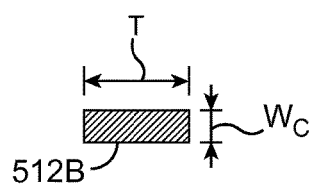
FIG. 4B is a cross-sectional view of a strut of the frame of FIG. 4A taken along line B-B therein.

FIGS. 3, 3A, 4 and 4A illustrate frame 210 in a deployed configuration removed from a remainder of prosthesis 200. FIGS. 3 and 4 are side views of frame 210, with FIG. 4 showing frame 210 rotated 90° about a longitudinal axis $L_A$ thereof from the orientation shown in FIG. 3. FIG. 3A is a top or inflow view of frame 210 taken in the direction of line A-A in FIG. 3 and FIG. 3B is a cross-sectional view of a strut 512B of frame 210 taken along line B-B in FIG. 3A. FIG. 4A is a sectional view of frame 210 taken along line A-A in FIG. 4 and FIG. 4B is a cross-sectional view of strut 512B of frame 210 taken along line B-B in FIG. 4A.

Frame 210 is a unitary structure that defines an inflow portion 202, a valve-retaining tubular portion 204 and a pair of support arms 206A, 206B. In the deployed configuration of frame 210, inflow portion 202 outwardly extends from a first or inflow end 203 of valve-retaining tubular portion 204 and support arms 206A, 206B backwardly extend from circumferentially spaced apart locations of an opposing second or outflow end 205 of valve-retaining tubular portion 204. When prosthesis 200 is implanted within a native mitral valve, inflow portion 202 of frame 210 is configured to engage an area of the left atrium that surrounds the native mitral valve, valve-retaining tubular portion 204 of frame 210 is configured to axially extend through the native mitral valve and thusly situates valve component 220 within the mitral valve annulus, and support arms 206A, 206B are configured to capture respective valve leaflets of the mitral valve and to secure them within the left ventricle without obstructing the outflow area of prosthesis 200 or the left ventricular outflow tract.

Figure 5:
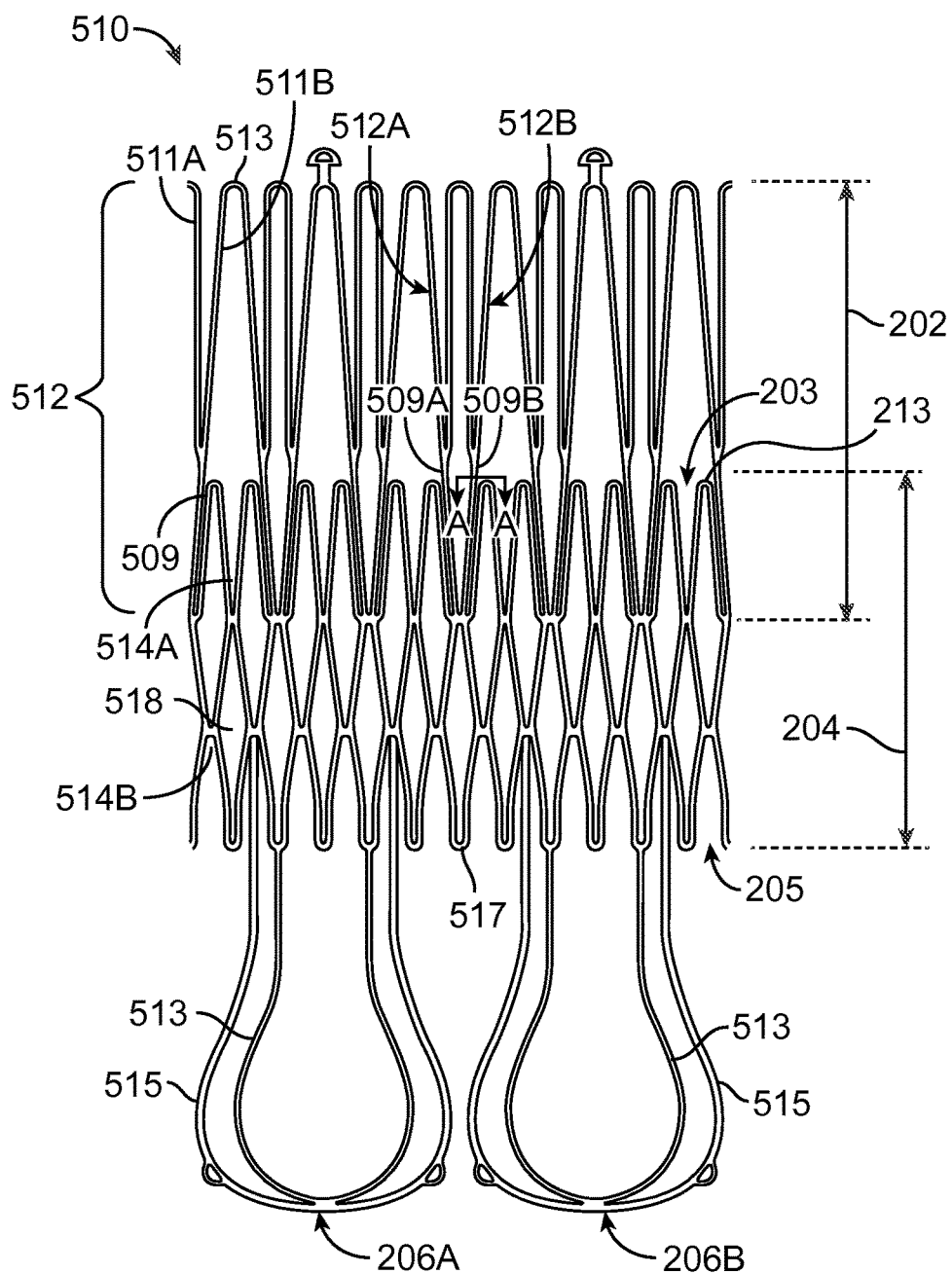
FIG. 5 depicts a patterned tube for forming the frame of FIGS. 3, 3A, 4 and 4A laid flat for illustrative purposes.

Frame 210 is a unitary structure, as previously noted above. In an initial step in manufacturing frame 210, a tube 510 of a suitable material is etched, cut or otherwise machined to have the pattern depicted in FIG. 5. FIG. 5 depicts for illustrative purposes only patterned tube 510 laid flat so that the cut structures of inflow portion 202, valve-retaining tubular portion 204 and support arms 206A, 206B may be more readily identified and described. Valve-retaining tubular portion 204 has a stent-like framework that defines diamond-shaped openings 518 and a series of upstream valleys 514A and downstream valleys 514B. Support arms 206A, 206B are formed from inner and outer looped struts 513, 515 with the outer looped struts 515 extending from spaced apart valleys 514B of valve-retaining tubular portion 204 and with the inner looped struts 513 extending from spaced apart downstream peaks 517 of valve-retaining tubular portion 204.

Figure 5A:
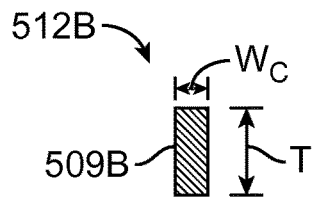
FIG. 5A is a cross-sectional view of the patterned tube of FIG. 5 taken along line A-A therein.

Inflow portion 202 is formed from a plurality of struts 512 having a cut width $W_C$ that is less than a thickness T thereof, as shown in FIG. 5A which is a cross-sectional view of strut 512B taken along line A-A in FIG. 5. Each strut 512 defines a base segment 509 and divergent first and second branch segments 511A, 511B. Accordingly, strut 512 may be considered to have a Y-shaped cut pattern. Base segments 509 of a respective pair of struts 512, for instance base segments 509A, 509B of struts 512A, 512B, extend from every other valley 514 at inflow end 203 of valve-retaining tubular portion 204. A plurality of crowns 513 are formed between first and second branch segments 511A, 511B of adjacent struts 512. Crowns 513 form radially outward ends of inflow portion 202 of frame 210, as shown in FIG. 3A. Circumferentially adjacent crowns 513 are not directly connected to each other and thereby provide inflow portion 202 with improved flexibility.

Subsequent processing steps are performed on patterned tube 510 in order to form frame 210 as shown in FIGS. 3, 3A, 4 and 4A. In one or more processing steps, patterned tube 510 is radially expanded to set a tubular shape and diameter of valve-retaining tubular portion 204 that is suitable for receiving valve component 220 therein. In one or more additional processing steps, support arms 206A, 206B are rotated outward and backward relative to outflow end 205 of valve-retaining tubular portion 204 and heat treated to set a shape thereof. In one or more additional processing steps, struts 512 of inflow portion 202 of patterned tube 510 are made to outwardly extend from inflow end 203 of valve-retaining tubular portion 204 and subjected to a forming process to have a substantially s-shaped profile, as best seen in FIG. 4A. In an embodiment and somewhat counter-intuitively, a first bend 416A and an opposing second bend 416B that form the substantially s-shaped profile of strut 512 are bent or curved over the cut width $W_C$ of the strut, as shown in FIGS. 3B and 4B, rather than being bent or curved over thickness T of the strut. First and second bends 416A, 416B of s-shaped strut 512 are able to be formed in this manner due to one or more twisted areas $TA_1$, $TA_2$, $TA_3$ of strut 512 that occur during formation of inflow portion 202. More particularly with reference to FIGS. 3A and 4A, base segment 509 of each strut 512 has a twisted area $TA_1$ near or adjacent to where the respective base segment 509 outwardly extends from inflow end 203 of valve-retaining tubular portion 204. Although not intending to be bound by theory, twisted area $TA_1$ turns cut width $W_C$ of the respective strut 512 approximately 90 degrees from the cut pattern shown in FIG. 5 such that the narrower portion Wc of the respective strut 512 is subjected to the forming process that creates first and second bends 416A, 416B. As well with reference to FIG. 3A, first and second branch segments 511A, 511B of each strut 512 have twisted areas $TA_2$, $TA_3$, respectively, near or adjacent to their respective crowns 513. Although not intending to be bound by theory, twisted areas $TA_2$, $TA_3$ turn cut width $W_C$ of the respective strut 512 in a direction opposite of twisted area $TA_1$ to return cut width $W_C$ to a similar orientation as shown in the cut pattern in FIG. 5, which results in cut width Wc facing inward and outward along at least a portion of first and second branch segments 511A, 511B of struts 512 and through crowns 513 of inflow portion 202.

Figure 6:
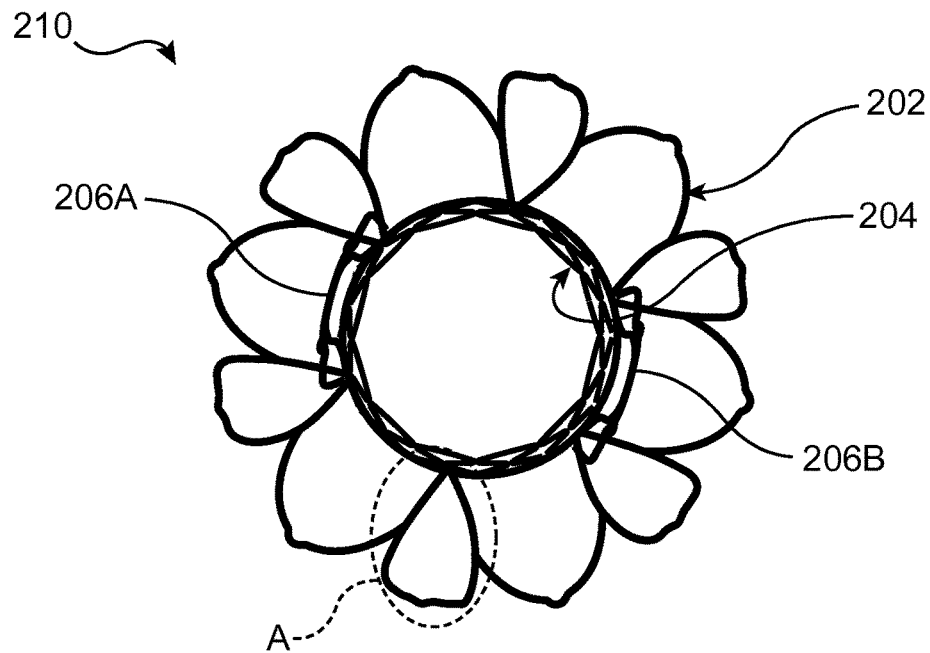
FIG. 6 is a photograph of an inflow area of a frame in accordance with the embodiment of FIGS. 3, 3A, 4 and 4A.
Figure 6A:
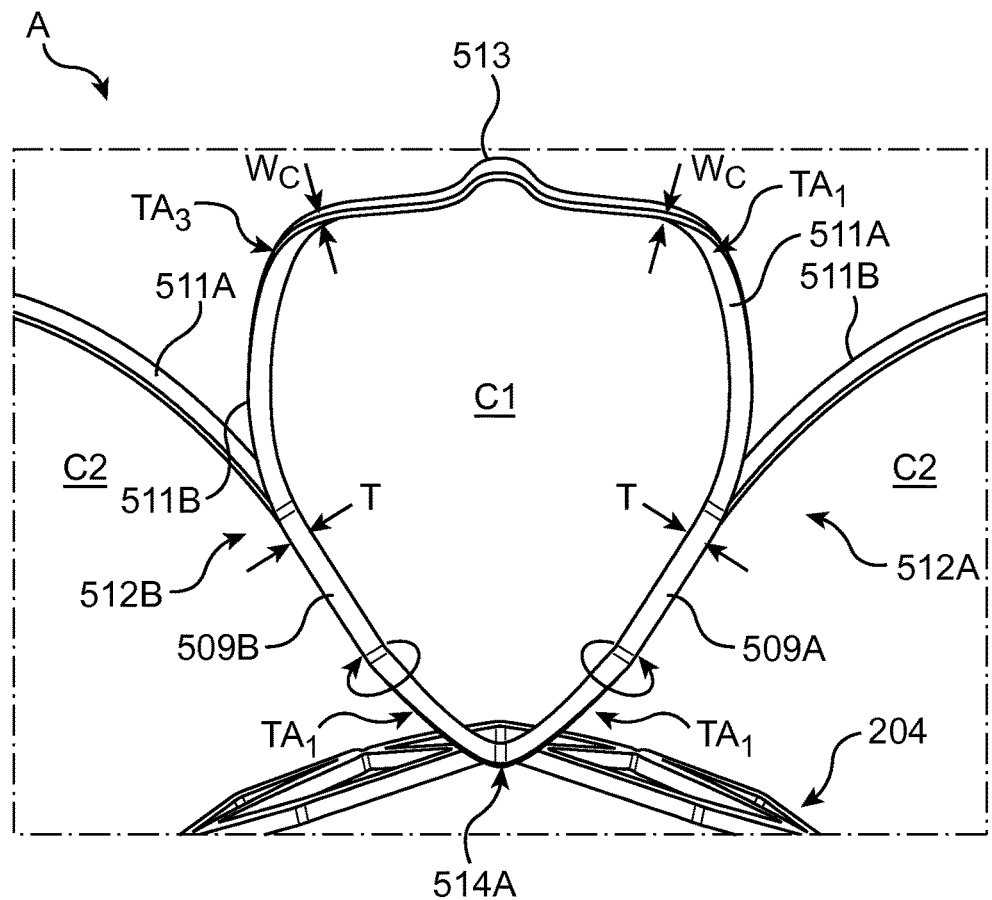
FIG. 6A is an enlarged view of an encircled area A of FIG. 6.

In the embodiment of frame 210 shown in FIGS. 3, 3A, 4 and 4A, inflow portion 202 may be described as having a ring of alternating openings or cells C1, C2 that are formed between respective portions of struts 512 and crowns 513. Cells C1, C2 have widths $W_1$, $W_2$, respectively, with width $W_1$ of cell C1 being less than width $W_2$ of cell C2, as best shown in FIG. 3A. Although not intending to be bound by theory, the alternating size of cells C1, C2 contributes to base segments 509 that emanate from a common valley 514 of tubular portion 204 having twisted areas $TA_1$ that twist or turn away from each other, or in other words twist in opposite directions from each other. For example with reference the pair of base segments 509A, 509B shown in FIGS. 3A, 6 and 6A, twisted area $TA_1$ of base segment 509A will turn strut 512A counterclockwise toward its adjacent cell C2, such that twisted area $TA_1$ of base segment 509A may be considered to have a left-hand twist, and twisted area $TA_1$ of base segment 509B will turn strut 512B clockwise toward its adjacent cell C2, such that twisted area $TA_1$ of base segment 509B may be considered to have a right-hand twist.

The s-shaped struts 512 that form inflow portion 202 of frame 210 act similarly to cantilever beams when interacting with the anatomy of the heart as a supporting and sealing structure of prosthesis 200. During the pressure changes and cyclical contractions of the heart, the s-shaped struts 512 are able to deflect while maintaining an axial force against the atrial surface of the heart that is sufficient for sealing and the prevention of paravalvular leakage between the frame and tissue surface. As well the combination of twisted areas $TA_1$, $TA_2$, $TA_3$ and s-shape of struts 512 of inflow portion 202 permit the inflow area of prosthesis 200 to readily deflect, flex and/or move during the cardiac cycle while also maintaining sufficient axial stiffness to provide sealing contact with the atrial surface that surrounds the implanted prosthesis. In addition, the twisted areas $TA_1$, $TA_2$, $TA_3$ of s-shaped struts 512 may reduce strain and improve the structural integrity of frame 210, and more particularly the structural integrity of inflow portion 202 thereof.

Figure 8:
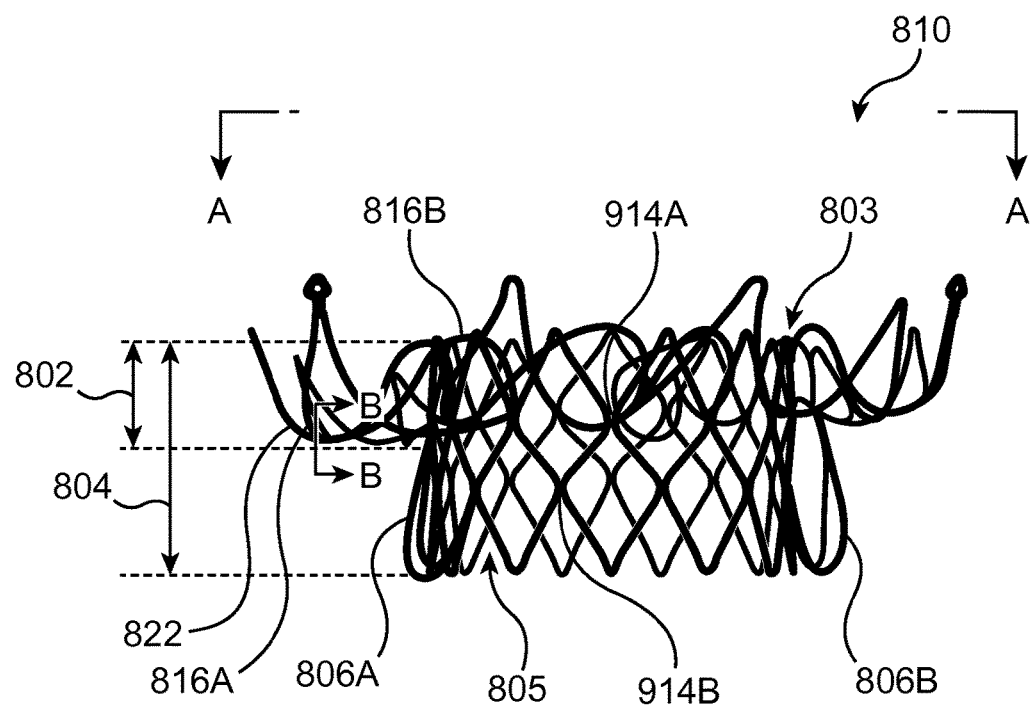
FIG. 8 is a photograph of a side of a frame in accordance with another embodiment hereof.
Figure 8A:
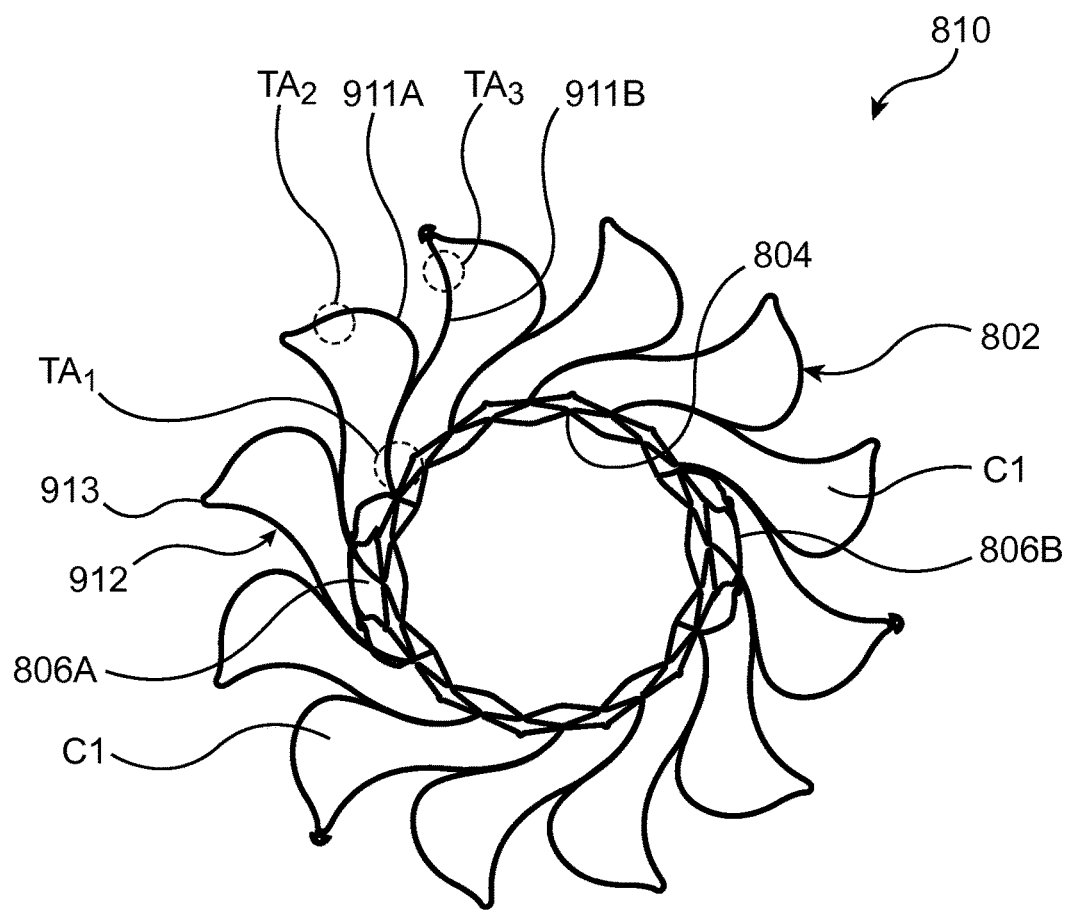
FIG. 8A is a photograph of an inflow area of the frame of FIG. 8 taken in the direction of line A-A therein.

FIGS. 8 and 8A illustrate a frame 810 in a deployed configuration in accordance with another embodiment hereof that is suitable for use in forming a mitral valve prosthesis similar to prosthesis 200 described above. FIG. 8 is a side view of frame 810, with FIG. 8A being a top or inflow view of frame 810 taken in the direction of line A-A in FIG. 8. Frame 810 is a unitary structure that defines an inflow portion 802, a valve-retaining tubular portion 804 and a pair of support arms 806A, 806B. In the deployed configuration of frame 810, inflow portion 802 outwardly extends from a first or inflow end 803 of valve-retaining tubular portion 804 and support arms 806A, 806B backwardly extend from circumferentially spaced apart locations of an opposing second or outflow end 805 of valve-retaining tubular portion 804. When implanted within a native mitral valve as a support structure of a mitral valve prosthesis, inflow portion 802 is configured to engage an area of the left atrium that surrounds the native mitral valve, valve-retaining tubular portion 804 is configured to axially extend through the native mitral valve and thusly situates a prosthetic valve component within the mitral valve annulus, and support arms 806A, 806B are configured to capture respective valve leaflets of the mitral valve and to secure them within the left ventricle without obstructing the outflow area of the prosthetic valve or the left ventricular outflow tract.

Figure 9:
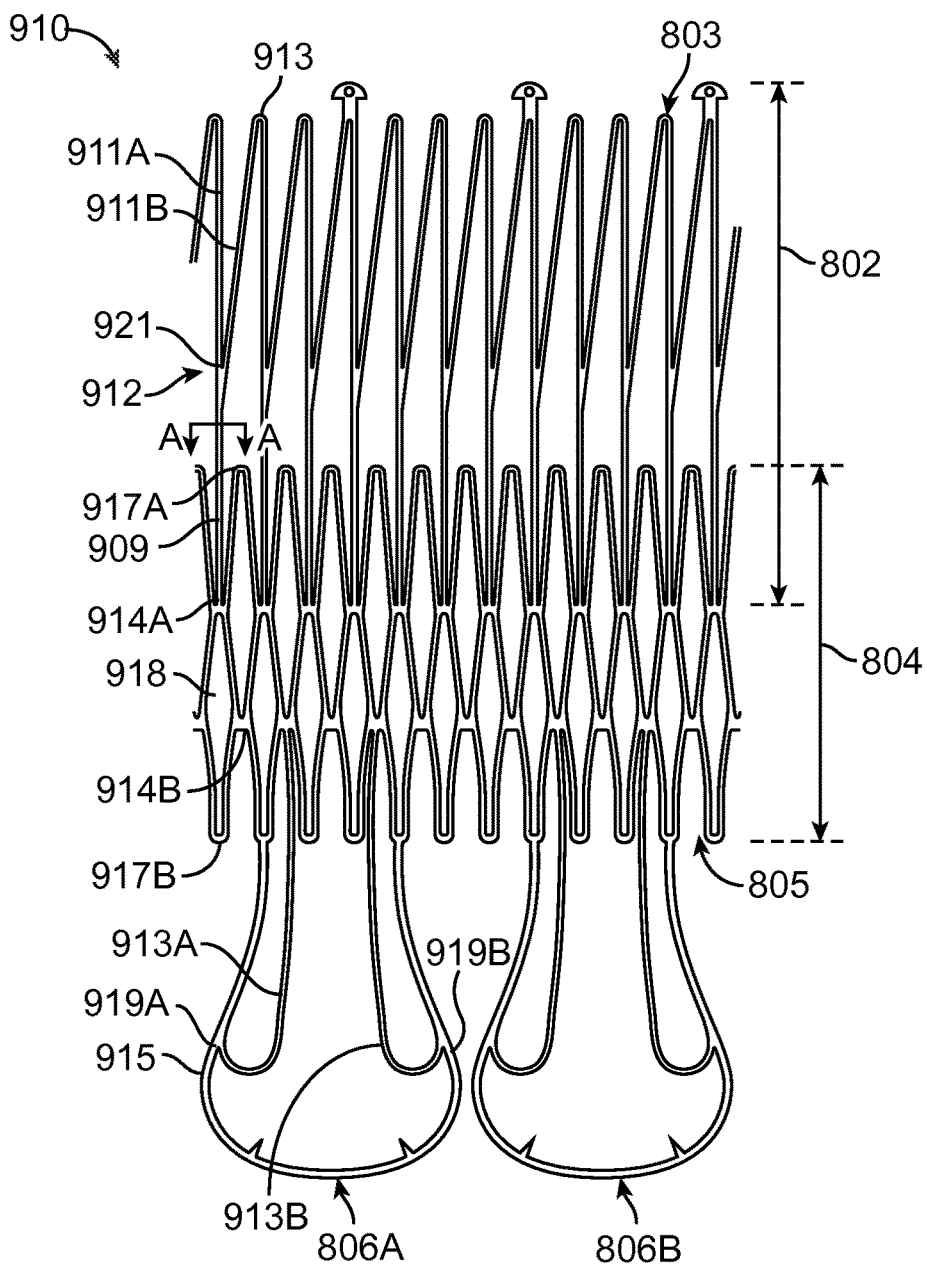
FIG. 9 depicts a patterned tube for forming the frame of FIGS. 8 and 8A laid flat for illustrative purposes.

In an initial step in manufacturing frame 810, a tube 910 of a suitable material is etched, cut or otherwise machined to have the pattern depicted in FIG. 9. FIG. 9 depicts for illustrative purposes only patterned tube 910 laid flat so that the cut structures of inflow portion 802, valve-retaining tubular portion 804 and support arms 806A, 806B may be more readily identified and described. Valve-retaining tubular portion 804 has a stent-like framework that defines diamond-shaped openings 918 and a series of upstream valleys 914A and downstream valleys 914B. Each support arm 806A, 806B is formed to have inner side struts 913A, 913B and an outer looped strut 915. Outer looped struts 915 extend from spaced apart downstream peaks 917B of valve-retaining tubular portion 804 and inner side struts 913A, 913B extend from respective downstream valleys 914B within their respective outer looped strut 915 and connect therewith at opposing interior locations 919A, 919B. In another embodiment in accordance herewith, tube 910 may be cut into a pattern such that frame 810 is formed to have support arms 206A, 206B as described with reference to the previous embodiment.

Figure 9A:
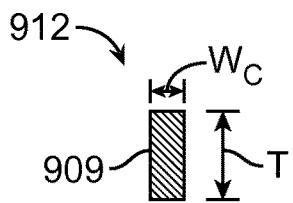
FIG. 9A is a cross-sectional view of the patterned tube of FIG. 9 taken along line A-A therein.

Inflow portion 802 is formed from a plurality of struts 912 having a cut width $W_C$ that is less than a thickness T thereof, as shown in FIG. 9A which is a cross-sectional view of a strut 912 taken along line A-A in FIG. 9. Each strut 912 defines a base segment 909 and first and second branch segments 911A, 911B, which diverge from base segment 909 at a respective node 921. Accordingly, strut 912 may be considered to have a Y-shaped cut pattern. A base segment 909 of a respective strut 912 extends from every upstream valley 914A at inflow end 803 of valve-retaining tubular portion 804. Each base segment 909 has a length that disposes a respective node 921 of strut 912 upstream of upstream peaks 917A. In an embodiment, base segment 909 has a length such that node 921 of strut 912 is disposed upstream of upstream peaks 917A by at least half a length of the base segment. Crowns 913 are formed between first and second branch segments 911A, 911B of adjacent struts 912. Crowns 913 form radially outward ends of inflow portion 902 of frame 910, as shown in FIG. 8A. Circumferentially adjacent crowns 913 are not directly connected to each other and thereby provide inflow portion 802 with improved flexibility.

Figure 8B:
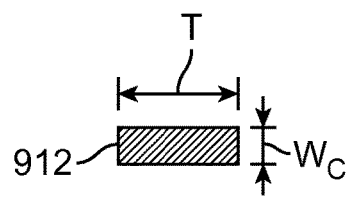
FIG. 8B is a cross-sectional view of a strut of the frame of FIG. 8 taken along line B-B therein.

Subsequent processing steps are performed on patterned tube 910 in order to form frame 810 as shown in FIGS. 8 and 8A. In one or more processing steps, patterned tube 910 is radially expanded to set a tubular shape and diameter of valve-retaining tubular portion 804 that is suitable for receiving a prosthetic valve component therein. In one or more additional processing steps, support arms 806A, 806B are rotated outward and backward relative to outflow end 805 of valve-retaining tubular portion 804 and heat treated to set a shape thereof. In one or more additional processing steps, struts 912 of inflow portion 802 of patterned tube 910 are made to outwardly extend from inflow end 803 of valve-retaining tubular portion 804 and subjected to a forming process to have a substantially s-shaped profile, as best seen in FIG. 8. Somewhat counter-intuitively, a first bend 816A and an opposing second bend 816B that form the substantially s-shaped profile of strut 912 are bent or curved over the cut width $W_C$ of the strut, as shown in FIG. 8B, rather than being bent or curved over thickness T of the strut. First and second bends 816A, 816B of s-shaped strut 912 are able to be formed in this manner due to one or more twisted areas $TA_1$, $TA_2$, $TA_3$ of strut 912 that occur during formation of inflow portion 802. More particularly with reference to FIG. 8A, base segment 909 of each strut 912 has a twisted area $TA_1$ near or adjacent to where the respective base segment 909 outwardly extends from inflow end 803 of valve-retaining tubular portion 804. Although not intending to be bound by theory, twisted area $TA_1$ turns cut width $W_C$ of the respective strut 912 approximately 90 degrees from the cut pattern shown in FIG. 9 such that the wider thickness T of the respective strut 912 is subjected to the forming process that creates first and second bends 816A, 816B. As well with reference to FIG. 8A, first and second branch segments 911A, 911B of each strut 912 have twisted areas $TA_2$, $TA_3$, respectively, near or adjacent to their respective crowns 913. Although not intending to be bound by theory, twisted areas $TA_2$, $TA_3$ turn cut width Wc of the respective strut 912 in a direction opposite of twisted area $TA_1$ to return cut width Wc to a similar orientation as shown in the cut pattern in FIG. 9, which results in cut width Wc facing inward and outward along at least a portion of first and second branch segments 911A, 911B of struts 912 and through crowns 913 of inflow portion 802.

In the embodiment of frame 810 shown in FIGS. 8 and 8A, inflow portion 802 may be described as having a ring of equal or like sized and shaped cells C1 that are formed between respective portions of struts 912 and crowns 913. In contrast to the symmetrical appearance of cells C1, C2 of inflow portion 202 of frame 210 shown in FIG. 4A, cells C1 of inflow portion 802 of frame 810 shown in FIG. 8A appear to spiral clockwise. Although not intending to be bound by theory, the spiral appearance of inflow portion 802 may be the result of all struts 912 having twisted areas $TA_1$ that twist or turn in a common or same direction from valve-retaining tubular section 804. In the embodiment shown in FIGS. 8 and 8A, the twisted area $TA_1$ of each base segment 909 turns the respective strut 912 clockwise relative to inflow end 803 of valve-retaining portion 804 such that twisted area $TA_1$ may be considered to have a right-hand twist. In another embodiment (not shown), the twisted area $TA_1$ of each base segment 909 turns the respective strut 912 counterclockwise relative to inflow end 803 of valve-retaining portion 804 such that twisted area $TA_1$ may be considered to have a left-hand twist.

Figure 7:
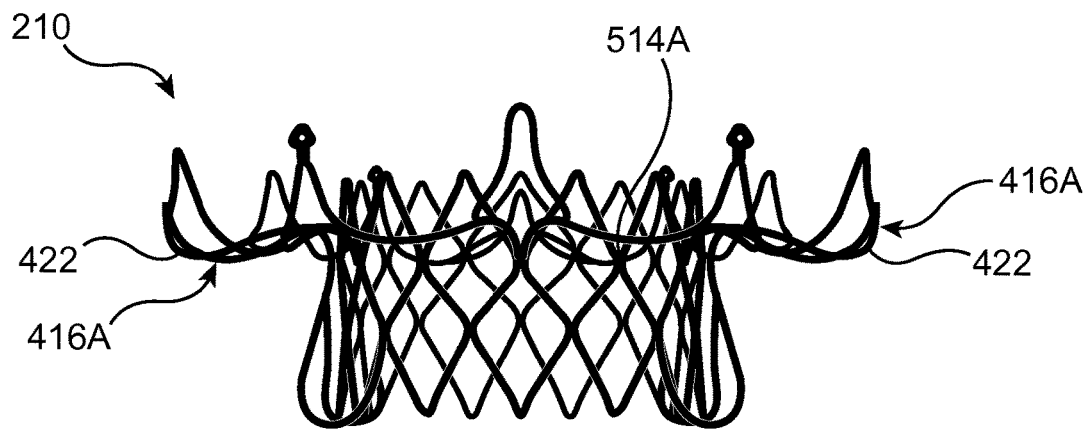
FIG. 7 is a photograph of a side of a frame in accordance with the embodiment of FIGS. 3, 3A, 4 and 4A.

With reference to FIG. 8, first bend 816A of each s-shaped strut 912 has an apex 822 that is longitudinally disposed at or near downstream valleys 914B of valve-retaining tubular portion 804. The increased depth of first bend 816A and the corresponding increased height of second bend 816B, as compared to first and second bends 816A, 816B, respectively, are made possible by the longer length of inflow struts 912 relative to an axial length of valve-retaining tubular portion 804 as compared to a length of inflow struts 512 relative to an axial length of valve-retaining tubular portion 204. In another embodiment, apex 822 of first bend 816A may be positioned at or near upstream valleys 914A of valve-retaining tubular portion 804, similar to the location of apex 422 of first bend 416A as shown in FIGS. 4 and 7. In other embodiments in accordance herewith, apex 822 of s-shaped struts 912 and apex 422 of s-shaped struts 512 may be suitably disposed anywhere along the axial length of valve-retaining tubular portions 204, 804, respectively, in order to tailor the flexibility of the respective inlet portion 202, 802 for a particular application.

Figure 10:
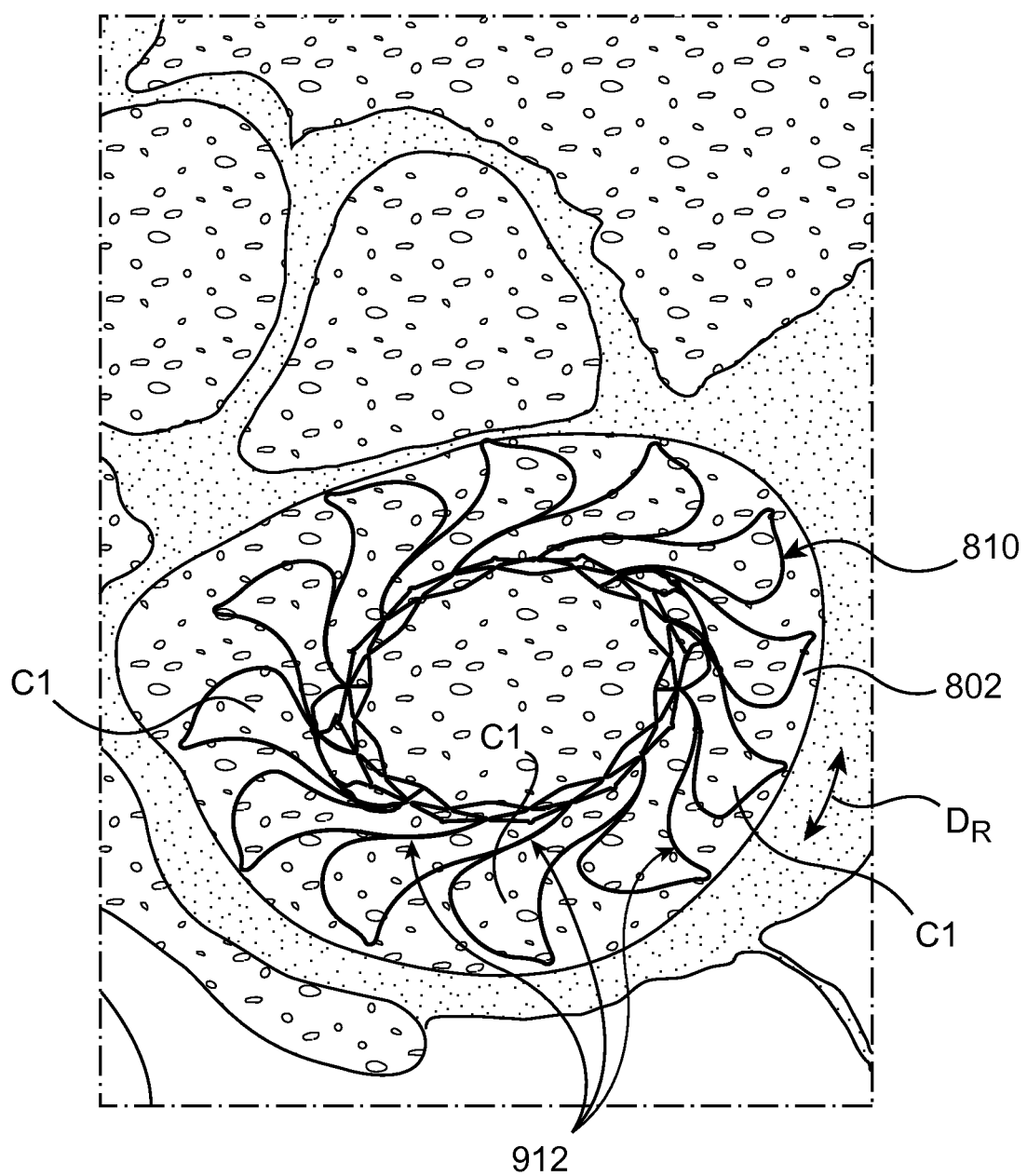
FIG. 10 is a photographic image of an implanted mitral valve prosthesis in accordance with an embodiment hereof.
Figure 11:
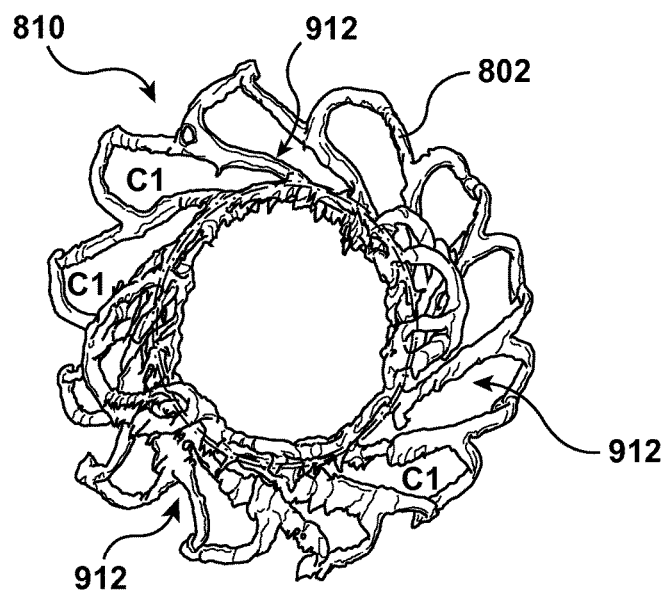
FIG. 11 shows an inflow portion of the frame of FIGS. 8 and 8A after implantation.
Figure 12:
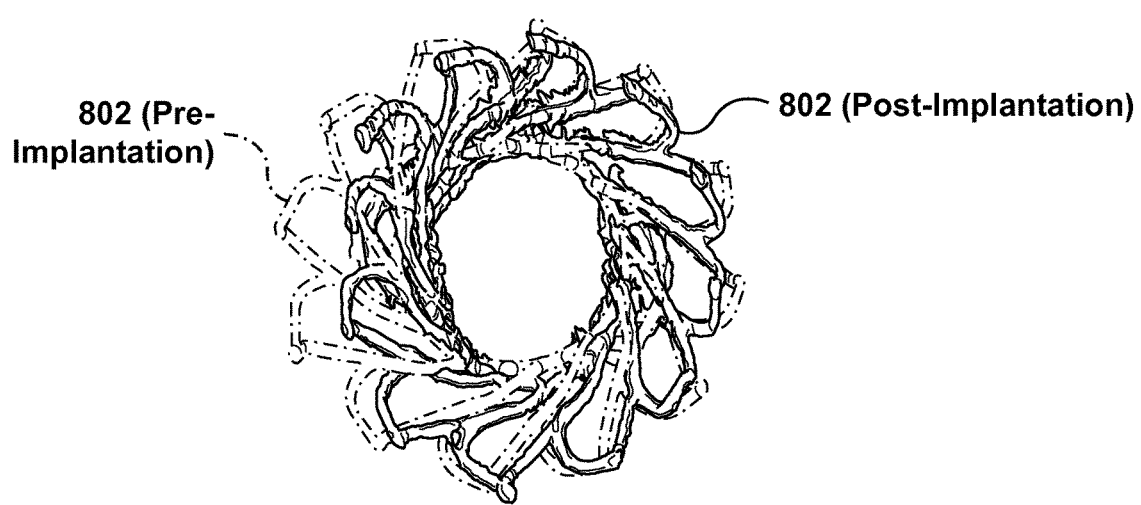
FIG. 12 shows the post-implantation inflow portion of the frame shown in FIG. 11 transposed on a pre-implantation inflow portion of the frame as shown in FIG. 8A.

The s-shaped struts 912 that form inflow portion 802 of frame 810 act similarly to cantilever beams when interacting with the anatomy of the heart as a supporting and sealing structure of a mitral valve prosthesis in accordance with embodiments hereof. During the pressure changes and cyclical contractions of the heart, the s-shaped struts 912 are able to deflect while maintaining an axial force against the atrial surface of the heart that is sufficient for sealing and the prevention of paravalvular leakage between the frame and tissue surface. As well the combination of twisted areas $TA_1$, $TA_2$, $TA_3$ and the s-shape of struts 912 of inflow portion 802 permit the inflow area of mitral valve prosthesis in accordance with embodiments hereof to readily deflect, flex and/or move during the cardiac cycle while also maintaining sufficient axial stiffness to provide sealing contact with the atrial surface that surrounds the implanted prosthesis. In addition, the twisted areas $TA_1$, $TA_2$, $TA_3$ of s-shaped struts 912 may reduce strain and improve the structural integrity of frame 810, and more particularly the structural integrity of inflow portion 802 thereof. Another benefit of the design of inflow portion 802 of frame 810 is that it readily conforms to the D-shape of the mitral valve annulus by allowing deflection or movement in a radial direction $D_R$ of struts 912 and the cells C1 defined thereby, as shown in FIGS. 10-12. FIG. 10 is a photographic image of an implanted mitral valve prosthesis having a frame 810 that shows how individual struts 912 have radially deflected or moved after implantation to "lay down" a bit flatter and conform to the D-shape of the native mitral valve annulus. This anatomically conforming feature of frame 810 is more clearly depicted in FIGS. 11 and 12, with FIG. 11 showing the deformation of inflow portion 802 of frame 810 after implantation and with FIG. 12 showing the post-implantation deformed inflow portion 802 of FIG. 11 (shown in cyan) transposed on a pre-implantation inflow portion 802 of FIG. 8A (shown in red).

In order to transform between an initial compressed configuration and the deployed configuration shown in the figures hereof, frames 210, 810 in accordance with embodiments described herein are formed from a self-expanding material that has a mechanical memory to return to the deployed configuration. Accordingly in accordance with embodiments hereof, frames 210, 810 may be made from stainless steel, a pseudo-elastic metal such as a nickel titanium alloy or nitinol, or a so-called super alloy, which may have a base metal of nickel, cobalt, chromium, or other metal. Mechanical memory may be imparted to the tubular structure that forms frames 210, 810 by thermal treatment to achieve a spring temper in stainless steel, for example, or to set a shape memory in a susceptible metal alloy, such as nitinol. Mitral valve prosthesis in accordance with embodiments hereof may be delivered via a transapical implantation procedure or via a transatrial implantation procedure. Suitable transapical and/or transatrial implantation procedures that may be adapted for use with mitral valve prosthesis described herein are disclosed in U.S. application Ser. No. 13/572,842 filed Aug. 13, 2012 to Igor Kovalsky, U.S. Appl. Pub. No. 2011/0208297 to Tuval et al., and U.S. Appl. Pub. No. 2012/0035722 to Tuval et al, each of which is incorporated by reference herein in its entirety.

In accordance with embodiments hereof, valve leaflets hereof, such as first and second valve leaflets 224A, 224B, may be made of or formed from a natural material obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. In accordance with other embodiments hereof, synthetic materials suitable for use as valve leaflets hereof, such as valve leaflets 224A, 224B, include DACRON® polyester commercially available from Invista North America S.A.R.L. of Wilmington, Del., other cloth materials, nylon blends, polymeric materials, and vacuum deposition nitinol fabricated materials. In an embodiment, valve leaflets hereof, such as valve leaflets 224A, 224B, can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

In accordance with embodiments hereof, graft material 226 or portions thereof may be a low-porosity woven fabric, such as polyester, DACRON® polyester, or polytetrafluoroethylene (PTFE), which creates a one-way fluid passage when attached to frame 210. In an embodiment, graft material 226 or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for graft material 226 or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 226 or portions thereof may be a natural material, such as pericardium or another membranous tissue.

In accordance with embodiments hereof, valve-retaining tubular portions and support arms of frames disclosed herein, as well as the graft material and tent-like structures that may be associated therewith, may be modified without departing from the scope of the present invention in view of the disclosures of one or more of U.S. application Ser. No. 13/736,460 filed Jan. 8, 2013 to Igor Kovalsky et al., U.S. Appl. No. 61/822,616 filed May 13, 2013 to Kshitija Garde et al., and U.S. application Ser. No. 13/572,842 filed Aug. 13, 2012 to Igor Kovalsky, each of which is incorporated by reference herein in its entirety.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A mitral valve prosthesis comprising:
a frame having an inflow portion, a valve-retaining tubular portion and a pair of support arms, the inflow portion radially extending from a first end of the valve-retaining tubular portion and the pair of support arms being circumferentially spaced apart and extending from an opposing second end of the valve-retaining tubular portion,
wherein the inflow portion is formed from a plurality of struts that outwardly extend from the first end of the valve-retaining tubular portion with adjacent struts of the plurality of struts being joined,
wherein each strut of the plurality of struts has a substantially s-shaped profile,
wherein each strut has a base segment joined to the valve-retaining tubular portion and wherein the base segment has a twisted area,
wherein each strut has first and second branch segments that diverge from the base segment and wherein each of the first and second branch segments has a respective twisted area, and
wherein a cut width of each of the twisted areas of the respective strut is turned one of clockwise or counterclockwise relative to an initial position of the cut width in a cut pattern of the frame.

2. The mitral valve prosthesis of claim 1, wherein adjacent struts of the plurality of struts are joined by respective crowns.

3. The mitral valve prosthesis of claim 2, wherein adjacent crowns are not directly attached to each other.

4. The mitral valve prosthesis of claim 1,
wherein twisted areas of the base segments of the plurality of struts are twisted in the same direction.

5. The mitral valve prosthesis of claim 1,
wherein the base segment of each strut radially extends from a respective valley at the first end of the valve-retaining tubular portion.

6. The mitral valve prosthesis of claim 1, wherein first and second branch segments of adjacent struts are joined to each other by a respective crown.

7. The mitral valve prosthesis of claim 1, wherein each strut has a first bend and an opposing second bend that form the substantially s-shaped profile thereof.

8. The mitral valve prosthesis of claim 7, wherein one of the first and second bends of each strut has an apex that is longitudinally disposed at or near downstream valleys of the valve-retaining tubular portion.

9. A mitral valve prosthesis comprising:
a frame having an inflow portion, a valve-retaining tubular portion and a pair of support arms, the inflow portion radially extending from a first end of the valve-retaining tubular portion and the pair of support arms being circumferentially spaced apart and extending from an opposing second end of the valve-retaining tubular portion,
wherein the inflow portion is formed from a plurality of struts that outwardly extend from the first end of the valve-retaining tubular portion with adjacent struts of the plurality of struts being joined,
wherein each strut of the plurality of struts has a substantially s-shaped profile and at least one twisted area,
wherein each strut has a base segment joined to the valve-retaining tubular portion and wherein the base segment has a twisted area,
wherein a pair of base segments radially extends from every other valley at the first end of the valve-retaining tubular portion, and
wherein the twisted area of a first base segment of each pair of base segments twists in an opposite direction from the twisted area of a second base segment of each pair of base segments.

10. A mitral valve prosthesis comprising:
a frame having an inflow portion, and a valve-retaining tubular portion, wherein in a deployed configuration the inflow portion of the frame radially extends from a first end of the valve-retaining tubular portion, and wherein the inflow portion of the frame is comprised of a plurality of struts with each strut forming a substantially s-shaped profile when radially extending from the first end of the valve-retaining tubular portion in the deployed configuration,
wherein each strut is Y-shaped having a base segment and first and second branch segments that diverge from the base segment,
wherein the base segment of each strut is joined to the valve-retaining tubular portion and wherein the base segment has a twisted area,
wherein each of the first and second branch segments of each strut has a respective twisted area, and
wherein a cut width of each of the twisted areas of the respective strut is turned one of clockwise or counterclockwise relative to an initial position of the cut width in a cut pattern of the frame.

11. The mitral valve prosthesis of claim 10, wherein adjacent struts of the plurality of struts are joined by respective crowns.

12. The mitral valve prosthesis of claim 11, wherein adjacent crowns are not directly attached to each other.

13. The mitral valve prosthesis of claim 10, wherein each strut has a first bend and an opposing second bend that form the substantially s-shaped profile thereof.

14. The mitral valve prosthesis of claim 13, wherein one of the first and second bends of each strut has an apex that is longitudinally disposed at or near downstream valleys of the valve-retaining tubular portion.

15. The mitral valve prosthesis of claim 10, wherein within each of the twisted areas the cut width of the respective strut is turned approximately ninety degrees from the position of the cut width in the cut pattern of the frame.

* * * * *